(12) United States Patent
Jeannotte et al.

(10) Patent No.: US 7,859,657 B2
(45) Date of Patent: Dec. 28, 2010

(54) METHODS OF MAKING AND USING AN APPARATUS AND DEVICES FOR PLACING LIGHT AND SAMPLE IN PHOTO-EMITTING OR ABSORBING DEVICES

(75) Inventors: Anthony Jeannotte, Foxborough, MA (US); Anthony C. Gilby, Foxborough, MA (US); Theodore Dourdeville, Marion, MA (US); Dennis DellaRovere, Mendon, MA (US); John Leason, Taunton, MA (US)

(73) Assignee: Waters Technologies Corporation, Milford, MA (US)

( * ) Notice: Subject to any disclaimer, the term of this patent is extended or adjusted under 35 U.S.C. 154(b) by 316 days.

(21) Appl. No.: 11/573,738

(22) PCT Filed: Aug. 17, 2005

(86) PCT No.: PCT/US2005/029204
§ 371 (c)(1),
(2), (4) Date: Jun. 22, 2007

(87) PCT Pub. No.: WO2006/023525
PCT Pub. Date: Mar. 2, 2006

(65) Prior Publication Data
US 2010/0026999 A1  Feb. 4, 2010

(51) Int. Cl.
*G01N 1/10* (2006.01)
(52) U.S. Cl. .................................... 356/246
(58) Field of Classification Search .......... 356/244–246
See application file for complete search history.

(56) References Cited
U.S. PATENT DOCUMENTS 6,188,813 B1 * 2/2001 Dourdeville et al. .......... 385/12
6,542,231 B1 * 4/2003 Garrett ....................... 356/246

* cited by examiner

*Primary Examiner*—Michael P Stafira
(74) *Attorney, Agent, or Firm*—Anthony J. Janiuk; Guerin Rodriguez LLP

(57) ABSTRACT

The present invention relates to apparatus and devices (11) for placing light with samples for analysis and method of making and using such apparatus and device.

13 Claims, 3 Drawing Sheets

METHODS OF MAKING AND USING AN APPARATUS AND DEVICES FOR PLACING LIGHT AND SAMPLE IN PHOTO-EMITTING OR ABSORBING DEVICES

CROSS REFERENCE TO RELATED APPLICATIONS

This application claims priority from U.S. Provisional Patent Application No. 60/602,535, filed Aug. 18, 2004. The contents of these applications are incorporated herein by reference.

STATEMENT REGARDING FEDERALLY FUNDED RESEARCH AND DEVELOPMENT

Not Applicable

FIELD OF THE INVENTION

Embodiments of the present invention relate to apparatus and devices that produce a signal corresponding with an interaction of light with a sample.

BACKGROUND OF THE INVENTION

Embodiments of the present invention relate to devices that use light for the purpose of analysis. These devices and apparatus are used as detectors. It is convenient to refer to light as comprised of photons and this application will use the terms light and photons interchangeably. In such devices light is introduced into a vessel containing a sample; light leaving the vessel is measured. The absence or diminution of light of a particular wavelength, present upon entry into the vessel suggests absorption of light by the sample or a constituent within the sample. The presence of light at an intensity or at a wavelength not present upon entry into the vessel suggests a shift in wavelength. These changes in the light entering and leaving a vessel are characteristic of the compounds in the sample.

The term "sample" is used in the broadest sense to indicate something that one wishes to evaluate. Samples can originate with industrial materials, chemical synthesis, or may have originated from biological sources.

Vessels which receive a flow of sample over time and subject such sample flow to light for analysis purposes are called optical flow cells. These vessels can comprise a length of conduit of similar dimensions or may represent a broadening or narrowing of the conduit. Such vessels typically will have inlets and outlets for sample and inlets and outlets for light.

Chromatography is the science of separations based on differences in affinity that different compositions have to an stationary phase. High performance liquid chromatography (HPLC) is performed in columns or cartridges. Solutions in which samples are dissolved are pumped through the columns or cartridges. The columns and cartridges conduits have an inert stationary phase. The components of the sample separate as they move through the stationary phase. It desirable to detect the separated components with a detector.

This application will use the term HPLC as referring to separations at pressures up to approximately 3,000 pounds per square inch (psi). At higher pressures, it is possible to perform sharper better defined separations with greater speed. However, higher pressures, referring now to the ultra high pressure range, approximately 4,000 psi to 15,000 psi, places extreme demands on equipment.

Mechanical stresses brought on by high sample pressures and the need for sample-wetted materials that resist the wide variety of HPLC solvents and samples can result in optical-fiber based flow cell designs that are difficult to manufacture. The end of a optical fiber placing light in or taking light out may need to be subjected to the ultra high pressure. The optical fiber, in these situations, is difficult to secure. The optical fiber must also be shielded from extraneous light. The flow cell vessel must also create a flow of sample in which all the sample is exposed to an equal amount of light; that is, there are no dead volumes. These difficulties are compounded by the small scale of the devices. It is desirable to have optical sensors which have small volumes.

SUMMARY OF THE INVENTION

Embodiments of the present invention are directed to devices, apparatus and methods of making and using such devices and apparatus that employ light detection or sensing methods for analysis. The devices and apparatus of the present invention are well suited for applications at high and ultra-high liquid chromatography pressures.

One embodiment of the present invention features a device for connecting an optical fiber to a high pressure containment vessel. The device comprises a housing having an exterior surface and an optical fiber bore. The optical fiber bore has a first opening and a second opening. The first opening is for receiving and substantially engaging in sealing relationship one end of a optical fiber to form a fiber optic coupling surface on the exterior surface of said housing. The second opening is for receiving the optical fiber extending from the first opening and for receiving a potting material to secure the optical fiber in the optical fiber bore.

As used herein, the phrase "substantially engaging in sealing relationship" means the opening with the optical fiber does not leak excessively when the potting material is placed in the optical fiber bore.

Preferably, the device further comprises an optical fiber substantially engaged in sealing relationship in said first opening. And, more preferably, the device comprises a potting material within said optical fiber bore to secure said fiber.

Preferably, the device further comprises an optical fiber sleeve. The optical fiber sleeve is a cylindrical form that extends into the optical fiber bore to align, position and protect the optical fiber. The sleeve also complements the potting material in effecting a bonding of the optical fiber to the fiber bore.

Particularly for flow cell applications, a preferred device has a housing having a least one capillary bore. The capillary bore has a first capillary opening and a second capillary opening. The first capillary opening is for receiving and substantially engaging in sealing relationship one end of a capillary to form a capillary coupling surface on the exterior surface of said housing. The second capillary opening is for receiving the capillary extending from the first capillary opening and for receiving a potting material to secure the capillary in the capillary bore.

As used herein, the term capillary is used in a broad sense to refer to any pipe or tube or conduit unless the context of the sentence requires otherwise. Embodiments of the present invention are ideally suited for capillary scale conduits. That is, conduits having extremely small diameters.

Preferably, the device further comprises a capillary engaged in sealing relationship in said first capillary opening. And, preferably, the device comprises a potting material within said capillary bore to secure said capillary. One preferred embodiment is a device further comprising a capillary sleeve. The capillary sleeve extending into the capillary bore to align, position and protect the capillary.

Embodiments of the present invention are directed to flow cells and optical connectors to flow cells. Preferably, the housing has a flow cell receiving surface about the capillary opening and the optical fiber opening for affixing to a flow cell. The optical fiber has a light path, defined by light passing through its length. The flow cell has a chamber for receiving or discharging fluid into the capillary opening and the chamber is constructed and arranged with respect to the light path to receive or pass light from the optical fiber.

Preferably, the device further comprises a gasket. The gasket is affixed to the flow cell receiving surface to convey fluids and seal gaps between the housing and the flow cell. Preferably, gasket has a channel between the capillary opening and the optical fiber opening to direct fluid into or receive fluid from the chamber. This feature is particularly useful where the chamber has a wall comprised of a material having a lower refractive index than aqueous solutions. Sample fluids in the life sciences are often aqueous solutions. In this case, the light is efficiently guided down the chamber due to total internal reflection. That is, the wall is comprised of a material with a refractive index less than 1.333 at 589 nm. The gasket has a gasket opening to allow the passage of light into the chamber. The gasket opening is aligned with the light path of the optical fiber. The gasket is comprised of an opaque or reflective material positioned in the flow cell along the light path in one or more of the of the following positions: a.) to block light leaving the optical fiber and entering the wall material and b.) to block light that may enter the wall material from subsequently entering the optical fiber.

Materials which exhibit a low refractive index include amorphous fluorocarbon polymers.

A further embodiment of the present invention is a device for placing light into a sample in the nature of a flow cell. The device comprises a sample containment vessel having a chamber for containing sample and receiving light traveling a light path. The chamber has at least one wall parallel to the light path having a layer of a material having a refractive index less than the sample fluid, to form a light guide. The chamber has a light entrance for receiving light. The light entrance has a rim of the material with the low refractive index. The device further comprises a gasket covering the rim. The gasket has a gasket opening to allow light to enter or leave the chamber via the optical fiber. The gasket is opaque or reflective and the opening sized to light to prevent light from entering the material from the optical fiber or the optical fiber from receiving light from the material. Light that has passed through the wall material and is subsequently detected by the light sensing means is known to alter the signal from the sample. Such effect diminishes detection sensitivity.

Preferably, the device has a chamber with single entrance for receiving sample and light. And, preferably, the gasket has a channel for transporting sample to or away from said entrance. Such gasket has a connector surface for receiving a optical fiber connector with means for introducing sample into the channel. Thus, the device, in the form of a flow cell is affixed to a optical fiber connector with the gasket interposed there between.

A further embodiment of the present invention is directed to a gasket. The gasket has a composition of a opaque or reflective material. The gasket is for sealing a connection between a connector and a containment vessel. The connector is for placing light and a sample in the containment vessel. The containment vessel is for holding sample while the sample is subjected to light. The connector has a first opening for receiving or discharging sample, and a light emitting or receiving end of a optical fiber. The containment vessel has a single entrance for receiving or discharging light and sample. The entrance has a rim of a material having a refractive index less than water. The gasket has a first planar surface and a second planar surface, a opening and channel means. The opening is for allowing the passage of light and sample into the chamber. The gasket opening is in communication with the channel means. The channel means is in at least one of the first planar surface and second planar surface. The channel is for placement in communication with the first opening and the end of said optical fiber. The gasket covers and shields the rim from light from the optical fiber or shields the optical fiber from light from the rim.

Preferably, the gasket further comprises keying means to align said gasket with one or more features of the connector and the containment vessel.

Preferably, the channel is a groove extending between the first opening and the end of the optical fiber. The end of the optical fiber also corresponds to the gasket opening.

Embodiments of the present invention also feature a method of making a connector for an optical fiber. The method comprises the steps of providing a housing having an exterior surface and an optical fiber bore. The optical fiber bore has a first opening and a second opening. The first opening is for receiving and substantially engaging in sealing relationship, one end of a optical fiber to form a fiber optic coupling surface on the exterior surface of the housing. The second opening is for receiving the optical fiber extending from the first opening and for receiving a potting material to secure the optical fiber in the optical fiber bore. The method further comprises the step of placing a optical fiber in the first opening and extending through the second opening. And, the method comprises the step of placing a potting material in the second opening and allowing said potting material to substantially fill the optical fiber bore to secure the optical fiber.

A preferred potting material is a polyarylketone and ethylenes, such as polyetheretherketone (PEEK). Other potting materials comprise polytrifluoroethylene (PTFE), polychlorotrifluoroethylene (PCTFE), perfluoroalkoxy (PFA), and fluoronated ethylenepropylene (FEP).

Preferably, the method further comprises the step of fitting an optical fiber sleeve into the optical fiber bore to align, position and protect said optical fiber prior to placing the potting material in the second opening.

Preferably, the method further comprises steps to secure capillaries and conduits. For example, without limitation, wherein the housing has a least one capillary bore, and the capillary bore has a first capillary opening and a second capillary opening, the first capillary opening receives and substantially engages in sealing relationship one end of a capillary to form a capillary coupling surface on the exterior surface of said housing. The second capillary opening receives the capillary extending from the first capillary opening. And, the method comprises the step of placing a potting material to secure the capillary in the capillary bore.

Preferably, the method further comprising the step of affixing a gasket to the housing or to the flow cell to which the housing will be attached. Preferably, the gasket has a channel, between the capillary opening and the optical fiber opening, to direct fluid or receive fluid from a chamber of a flow cell.

And, preferably, the chamber has a wall comprised of a material having a lower refractive index than aqueous solutions. The gasket is preferably comprised of an opaque or reflective material positioned along the light path. The gasket preferably blocks the light from traveling from the optical fiber from entering the material or blocks light traveling through the material from entering the optical fiber. Materials with low refractive indexes material include several amorphous fluorocarbon polymers.

Thus, embodiments of the present invention include methods of preventing stray light from entering a flow cell or from being discharged from a flow cell. Such method comprises the steps of providing a flow cell having a sample containment vessel. The vessel has a chamber for containing sample and receiving light traveling a light path. The chamber has at least one wall parallel to the light path having a layer of a material having a refractive index less than water to form a light guide. The chamber has a light entrance for receiving light with the entrance having a rim of the material. The method further comprises the step of fitting a gasket to cover the rim. The gasket is opaque or reflective to the light to prevent light from entering the material or from leaving the material.

These and other features and advantages of the present invention will be understood by individuals skilled in the art upon viewing the drawings and reading the detailed description of the invention that follows.

DETAILED DESCRIPTION OF THE INVENTION

Embodiment of the present invention will be described in detail as methods, devices and apparatus for transmitting light into or receiving light exiting a vessel. Embodiments have particular application in situations in which the vessel contains fluid under high pressure. Optical fibers are difficult to secure and maintain optical transparency. Individuals skilled in the art will readily appreciate that the present invention has broad applications to situations where it is desirable to secure optical fibers for other purposes as well.

Figure 1:
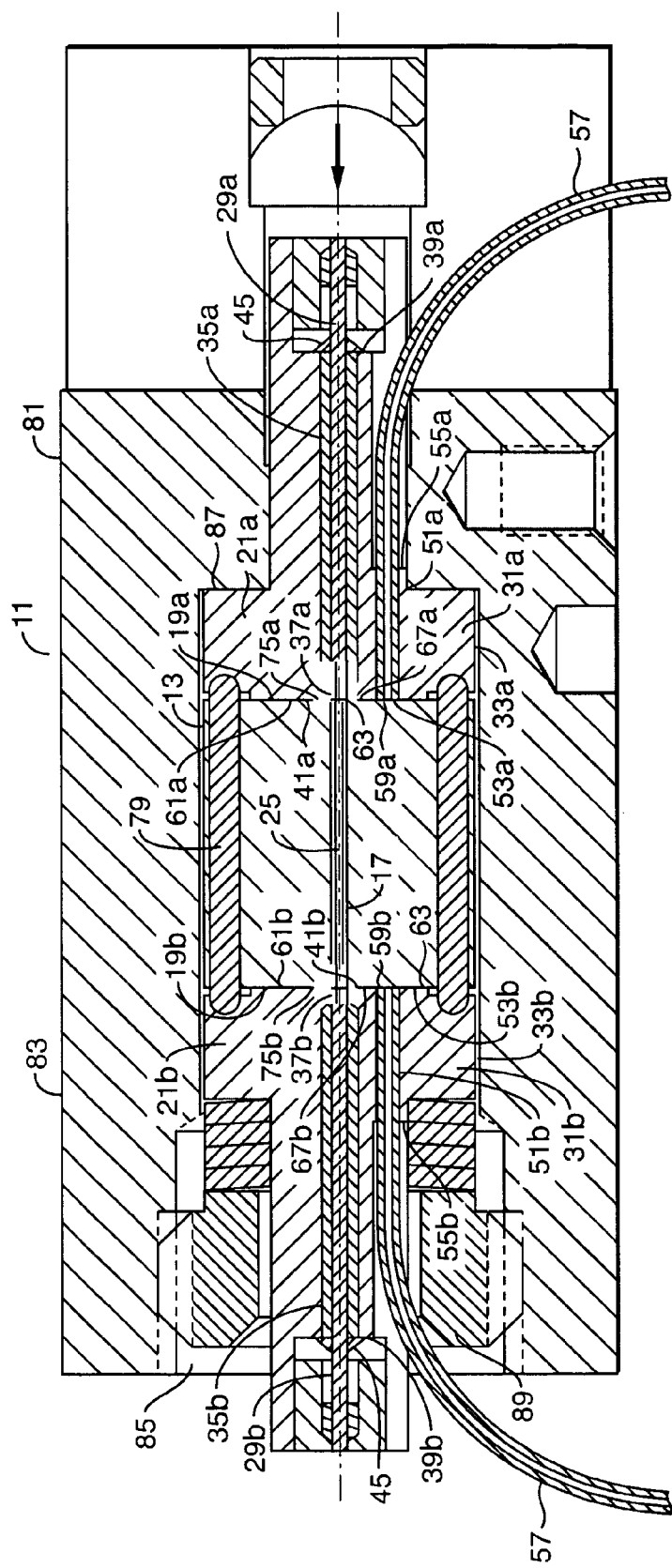
FIG. 1 depicts, in cross section, an apparatus for placing light in a sample embodying features of the present invention.

Turning first to FIG. 1, an apparatus, in the form of a flow cell, that embodies features of the present invention, is depicted generally designated by the numeral 11. The apparatus 11 has the following major elements: a vessel 13, vessel wall 17, first gasket 19a, second gasket 19b, and a first connector device 21a and a second connector device 21b.

The vessel wall 17 defines a chamber 25 for containing fluid, such as sample, under pressure. Embodiments of the present invention can withstand pressures greater than 4,000 psi and up to 15,000 psi. Light and sample are introduced into and taken out of the chamber 25 through at least one of the first connector device 21a and second connector device 21b.

First connector device 21a and second connector device 21b are identical to facilitate the manufacture of the flow cell 11. First connector device 21a and second connector device 21b are for connecting optical fibers 29a and 29b respectively to vessel 13. Each first connector device 21a and second connector device 21b has a connector housing 31 having an exterior surface 33 and an optical fiber bore 35.

Figure 2:
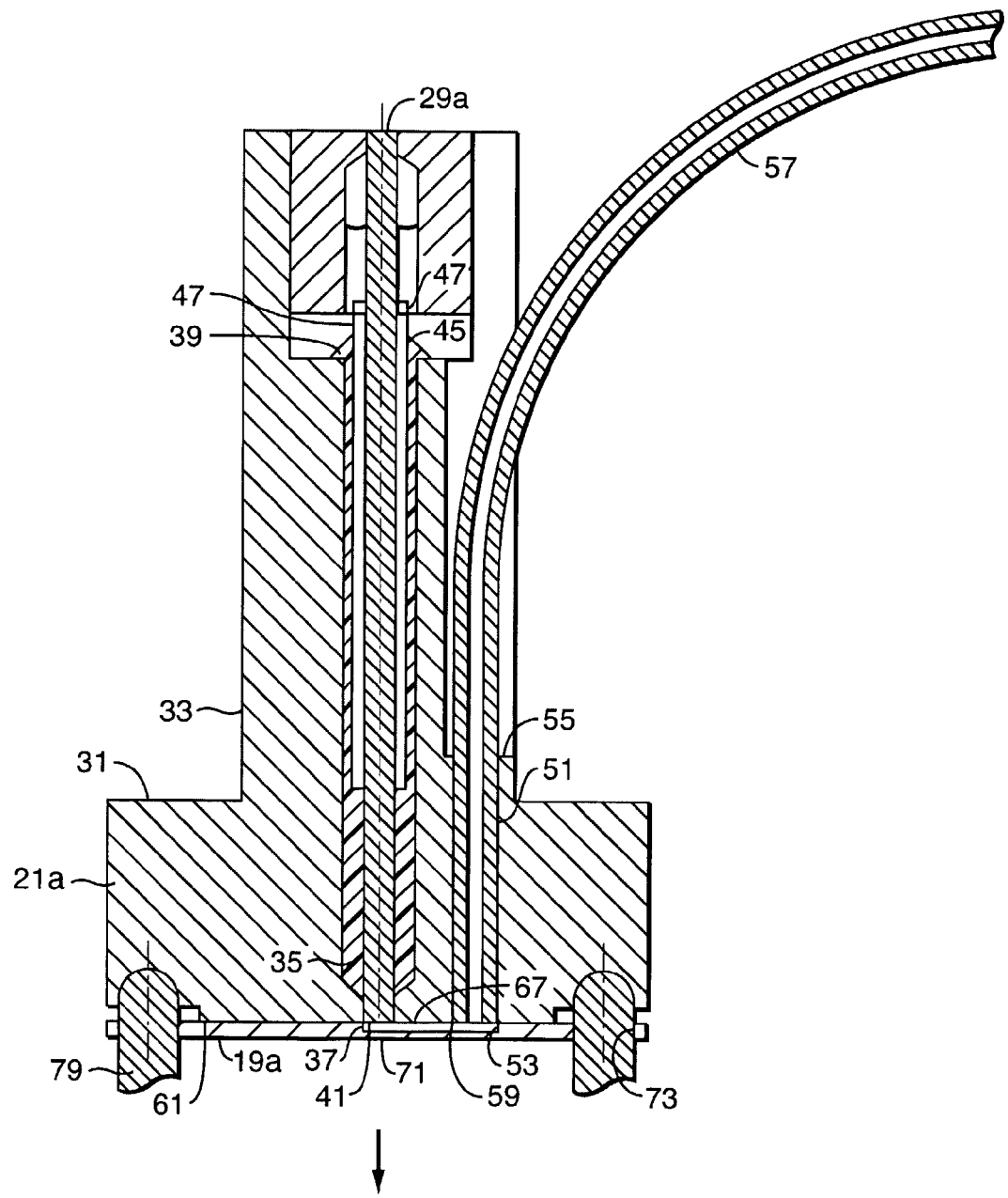
FIG. 2 depicts, in cross section, a connector embodying features of the present invention.

This discussion will describe first connector 29a in detail for the purpose of clarity with the understanding the discussion applies to second connector 29b as well. Turning now to FIG. 2, first connector device 21a has a housing 31 shown in cross section. Housing 31 has a optical fiber bore 35 having a first opening 37 and a second opening 39. The first opening 35 is for receiving and substantially engaging in sealing relationship one end of optical fiber 29a. A fiber optic coupling surface 41 is formed on the exterior surface 33 of said housing 31. There are well-known techniques such as optical polishing for producing a high quality optical finishes on the fiber coupling surface 41.

Preferably, the housing 31 is made of metal or rigid plastics. A preferred material is stainless steel. The dimensions will be influenced by the size of the vessel 15. A typical size is approximately 0.3 to 0.6 inches in diameter and similar dimensions in depth. The housing 31 fits to a vessel 13 appropriately sized in diameter and approximately 10 mm in length.

Returning now to FIG. 1, the second opening 39 is for receiving the optical fiber 29a extending from said first opening 37. A potting material 45 in optical fiber bore 35 secures the optical fiber 29a. Receiving and substantially engaging in sealing relationship, with respect to the optical fiber 29a in first opening 37 means that the potting material 45 does not leak excessively during the potting operation.

Preferably, during the potting operation, the potting material 45 is placed around the optical fiber 29a. The optical fiber 29a is in place or is placed in the first opening 37 with the potting material 45 and the housing heated to a temperature that allows the potting material 45 to flow and occupy optical fiber bore 35.

Preferably, the connector device 21a has a optical fiber sleeve 47 as best seen in FIG. 2. Optical fiber sleeve 47 has a cylindrical shape with an exterior diameter less than the optical fiber bore 35 and greater than the diameter of the optical fiber 29a. Optical fiber sleeve 47 is placed into said optical fiber bore 35 and receives optical fiber 29a and potting material 45 to align, position and protect the optical fiber 29a.

The connector device 21a has a least one capillary bore 51. Capillary bore 51 has a first capillary opening 53 and a second capillary opening 55. First capillary opening 53 is for receiving and substantially engaging in sealing relationship one end of a capillary 57 to form a capillary coupling surface 59 on the exterior surface 33 of housing 31. The second capillary opening 55 is for receiving capillary 57 extending from said first capillary opening 53. Capillary 57 can be sized to tightly fit the capillary bore 51 and be able to withstand pressures of greater than 4,000 psi and up to 15,000 psi.

For some applications it may be useful to increase the size of capillary bore 51 and second capillary opening 55 for receiving a potting material [not shown] in the manner described with respect to the optical fiber bore 35, to secure the capillary 55 in the capillary bore 51. And, for some applications, it is useful to use a capillary sleeve [not shown] in the manner of the optical fiber sleeve 47. The capillary sleeve is a cylindrical form sized with an exterior diameter less than the capillary bore 51 and an interior diameter greater than the diameter of the capillary 57, the capillary sleeve extending into the capillary bore to align, position and protect the capillary.

Housing 31 has a flow cell receiving surface 61 about the capillary first opening 53 and said optical fiber first opening 37 for affixing to a flow cell vessel 15. Turning now to FIG. 1, flow cell 15 has a corresponding housing receiving surface 63a and 63b for connector device 21a and 21b respectively. The optical fiber 29a has a light path on axis (illustrated with arrows) and optical fiber 29b receives light along a light path after such light has traversed chamber 25. Sample in the chamber 25 will alter the nature of the light received by optical fiber 29b.

Chamber 25 is in fluid communication with capillaries 57a and 57b of the first connector device 21a and second connector device 21b to receive and discharge sample fluid. First gasket 19a is interposed between the vessel 15 at housing receiving surface 63a and flow cell receiving surface 61a. Similarly second gasket 19b is interposed between the vessel 15 at housing receiving surface 63b and flow cell receiving surface 61b. First gasket 19a and second gasket 19b convey fluids and seal gaps between the housings 31 of connector devices 21a and 21b and the flow cell.

At least one of the first gasket 19a, second gasket 19b, flow cell receiving surface 61 and housing receiving surface 63 have channel means to convey fluid between the respective capillary 57a or 57b and chamber 25. A preferred channel means is a channel 67a and 67b in first gasket 19a and second gasket 19b respectively.

Figure 3:
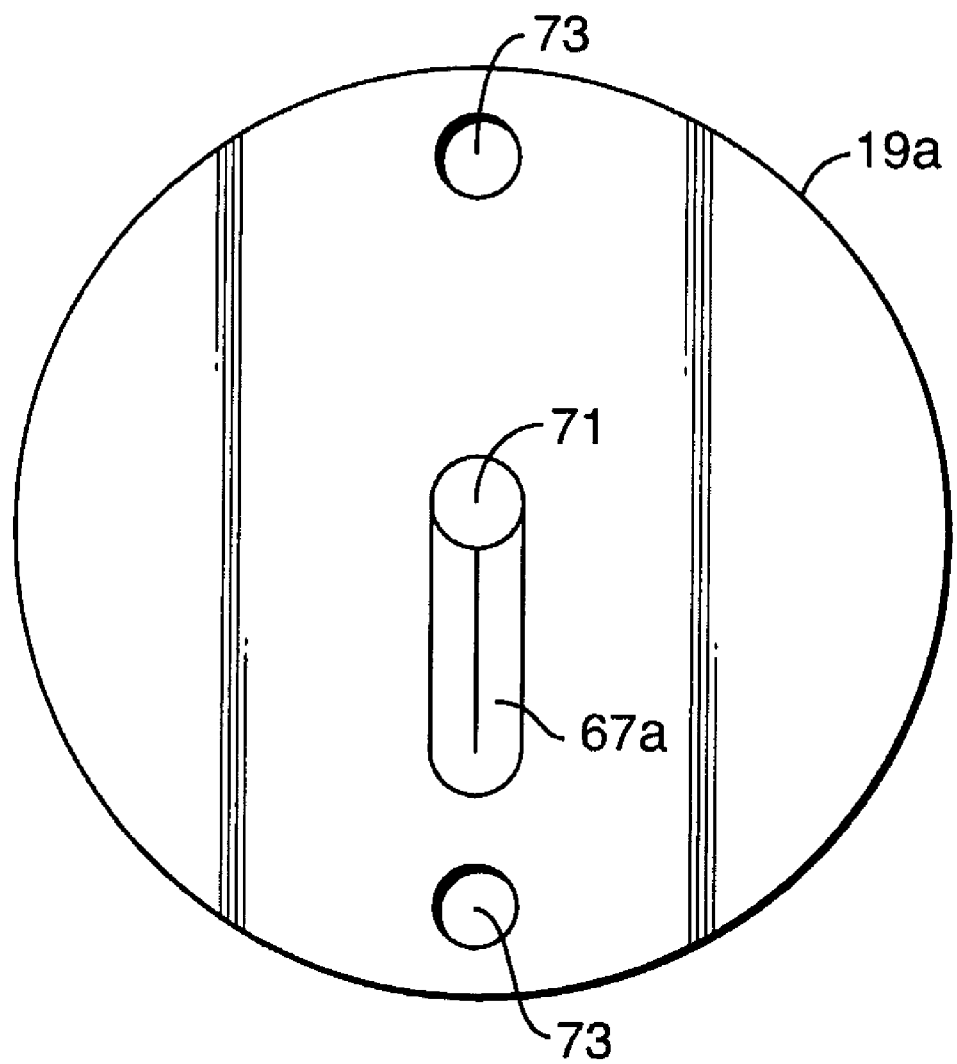
FIG. 3 depicts a top view of a gasket embodying features of the present invention.

Turning now to FIG. 3, gasket 19a has a light opening 71 and a channel 67a. The groove 67a extends to a position in communication with capillary opening. Gasket 19a is intended to be positioned with the channel 67a against the flow cell receiving surface 61 of the connector housing 31. However, in the event it is desired to place channel 67a against the housing receiving surface 63 or the vessel 15, a sample opening [not shown] is provided in gasket 19a. In order to align the channel 67a and opening 71, gasket 19a has keying means in the nature of holes 73. Holes 73 cooperate with pins 79 as best seen in FIG. 1.

In the alternative, channel means in the form of a groove [not shown] can be provided in the flow cell receiving surface 61, or the housing receiving surface 63 in which case the gasket 19a can omit the channel 67a. Thus, the vessel 15 receives light and sample through a single entrance, and discharges light and sample through a single exit.

The chamber 25 of vessel 15 has a wall 17 of cylindrical form in which the cylinder axis is aligned with the light path. The wall 17 has a composition having a lower refractive index than aqueous solutions. One such material is an amorphous fluorocarbon polymer. One such material is sold under the trademark Teflon AF (Dupont). The wall having a low refractive index reflects light impinging on the wall 17 back into the chamber 25. The wall 17 extends the length of the vessel 15 and forms a first rim 75a and a second rim 75b at the edges. Light entering the first rim 75a can interfere with the signal generated by the flow cell 11. Light exiting the second rim 75b also interferes with the signal.

First gasket 19a and second gasket 19b are comprised of an opaque material. A preferred material is a metal capable of being readily etched to provide a channel. First gasket 19a is positioned along the light path to block the light from traveling from said optical fiber 29a from entering material of which wall 17 is made. Second gasket 19b is positioned along the light path to block light traveling through the material from entering the optical fiber 29b. Optical fiber 29b would normally in communication with a photon detector [not shown].

The flow cell 11 further comprises a pressure assembly 81. Pressure assembly 81 has base 83 having a hollow 85 having an abutment ridge 87 for receiving second connector 21. Second gasket 19b, vessel 17, first gasket 19a, and first connector 19a are stacked within the hollow 85. Affixing means in the form of a nut 89 compresses the elements held in hollow 85 to effect sealing. The flow cell 11 can receive sample at pressures of 4,000 psi and up to 15,000 psi.

Thus, we have described an apparatus for placing light into a sample. The apparatus has a vessel 15 having a chamber 25 for containing sample and receiving light traveling a light path. The chamber 25 has at least one wall 17 parallel to said light path having a layer of a material having a refractive index less than water to form a light guide. The chamber 25 has a light entrance in the form of optical fiber 29a for receiving light at the entrance having a rim 75 of the material. A first gasket 19a, opaque or reflective to the light, covers the rim 75a to prevent light from entering said material. A second gasket 19b, opaque or reflective to light, covers the rim 75b to prevent light from entering second optical fiber 29b.

The flow cell 11 has a chamber 25 in which sample and light have a common entrance through first gasket 19a having a channel 67a for transporting sample to the chamber 25. Similarly the flow cell 11 has a chamber 25 in which sample and light have a common exit through a second gasket 19b having a channel 67b for transporting sample from the chamber 25.

Thus, we have disclosed a method of making a first connector 21a and second connector 21b for optical fiber 29a and 29b respectively. The method comprises the steps of providing a housing 31 having an exterior surface 33 and an optical fiber bore 35. The optical fiber bore 35 has a first opening 37 and a second opening 39. The first opening 37 is for receiving and substantially engaging in sealing relationship one end of a optical fiber 29a to form a fiber optic coupling surface 41 on the exterior surface 33 of the housing 31. The second opening 39 is for receiving the optical fiber extending from said first opening 37 and for receiving a potting material 45 to secure said optical fiber 29 in the optical fiber bore 35. The method further comprises the step of placing a optical fiber 29 in the first opening 37 and extending through said second opening 39 and placing a potting material 45 in the second opening 39 and allowing the potting material 45 to substantially fill the optical fiber bore 35 to secure the optical fiber 29.

The method may be extended to capillaries wherein said housing 31 has a least one capillary bore 51. The capillary bore 51 has a first capillary opening 53 and a second capillary opening 55. The method further comprising the steps of placing a capillary 57 in the first capillary opening 53 and extending through the second opening 55 and placing a potting material 45 in the second capillary opening 55 to secure the capillary 57.

Thus, we have disclosed a method of preventing stray light from entering a chamber 25 of a flow cell 11 or from being discharged from a chamber 25 of a flow cell 11. The method comprises the steps of fitting a first gasket 19a or a second gasket 19b to cover a rim 75a or 75b respectively.

We have disclosed preferred embodiment of the present invention which embodiments are capable of modification and alteration without departing from the teaching and spirit of the invention. Thus, the present invention should not be limited to the precise detail herein but should encompass the subject matter of the following claims and their equivalents.

What is claimed is:

1. A device for exposing a sample to light comprising:
a sample containment vessel having a chamber for containing said sample and receiving light traveling along a light path, said chamber having at least one wall parallel to said light path and comprising a layer of a material having a refractive index less than a refractive index of water to thereby form a light guide, said chamber having a light entrance for receiving light, said light entrance having a rim comprising said material; and
a gasket covering said rim, and being opaque or reflective to said received light to prevent stray light from entering said chamber via said material, said gasket having an opening aligned with said light entrance and a channel in communication with said opening for transporting said sample to or away from said light entrance, said channel extending along an outermost surface of said gasket abutting said rim of said chamber.

2. The device of claim 1 wherein said chamber has a single sample and light entrance.

3. The device of claim 1 wherein said gasket has a connector surface for receiving an optical fiber connector.

4. The device of claim 1 wherein said optical fiber connector has means for introducing said sample into said channel.

5. The device of claim 4 further comprising an optical fiber connector affixed to said sample containment vessel with said gasket interposed there between.

6. A gasket having a composition of an opaque or reflective material for sealing a connection between a connector and a containment vessel, said connector providing light and a sample to the containment vessel, said containment vessel configured to hold said sample while said sample is subjected to said light, said connector having a first opening for exposing a light emitting or receiving end of an optical fiber to said sample, said containment vessel having a single entrance for receiving or discharging light and said sample, said entrance having a rim comprising a material having a refractive index less than a refractive index of water, said gasket comprising:

a first planar surface;

a second planar surface; and channel means in at least one of said first planar surface and second planar surface, and being in communication with said first opening of said connector and said end of said optical fiber, the other of said first and second planar surfaces of said gasket covering and shielding said rim of said entrance of said containment vessel from light from said optical fiber or shielding said optical fiber from light from said rim.

7. The gasket of claim 6 further comprising keying means to align said gasket with said entrance of said containment vessel.

8. The gasket of claim 6 wherein said channel is a groove extending between said first opening and said end of said optical fiber.

9. A method of preventing stray light from entering a flow cell or from being discharged from a flow cell comprising:

providing a flow cell having a sample containment vessel, said vessel having a chamber for containing a sample and receiving light traveling along a light path, said chamber having at least one wall parallel to said light path having and comprising a layer of a material having a refractive index less than a refractive index of water to thereby form a light guide, said chamber having a light entrance for receiving light, said light entrance having a rim comprising said material; and fitting a gasket to cover said rim, said gasket opaque or reflective to said light to prevent stray light from entering said chamber via said material or from leaving said chamber via said material, said gasket having an opening aligned with said light entrance and a channel in communication with said opening for transporting said sample to or away from said light entrance, said channel extending along an outermost surface of said gasket abutting said rim of said chamber.

10. The method of claim 9 wherein said chamber has a single sample and light entrance.

11. The method of claim 9 wherein said gasket has a connector surface for receiving an optical fiber connector.

12. The method of claim 11 wherein said optical fiber connector has means for introducing the sample into said channel.

13. The method of claim 9 wherein said gasket has keying means to align said gasket with said entrance of said containment vessel.

* * * * *